United States Patent [19]

Marans et al.

[11] 4,061,662

[45] Dec. 6, 1977

[54] REMOVAL OF UNREACTED TOLYLENE DIISOCYANATE FROM URETHANE PREPOLYMERS

[75] Inventors: Nelson Samuel Marans; Alfred Gluecksmann, both of Silver Spring, Md.

[73] Assignee: W. R. Grace & Co., New York, N.Y.

[21] Appl. No.: 695,344

[22] Filed: June 14, 1976

Related U.S. Application Data

[63] Continuation of Ser. No. 608,498, Aug. 28, 1975, abandoned.

[51] Int. Cl.$^2$ ................ C07C 119/042; C07C 125/04
[52] U.S. Cl. ............................. 560/26; 260/2.5 AT; 260/454; 260/389; 260/455 A; 560/158
[58] Field of Search .......... 260/471 C, 453 SP, 482 B

[56] References Cited

U.S. PATENT DOCUMENTS 3,415,790  12/1968  Davis et al. ................ 260/453 X

FOREIGN PATENT DOCUMENTS 1,417,075  12/1975  United Kingdom .......... 260/453 SP

*Primary Examiner*—Dolph H. Torrence
*Attorney, Agent, or Firm*—Philip M. Pippenger; William W. McDowell, Jr.

[57] ABSTRACT

A process is described which is effective in removing unreacted tolylene diisocyanate (TDI) from a polyisocyanate by bringing said polyisocyanate into contact with molecular sieves.

16 Claims, No Drawings

REMOVAL OF UNREACTED TOLYLENE DIISOCYANATE FROM URETHANE PREPOLYMERS

This application is a continuation in part of application Ser. No. 608,498 filed Aug. 28, 1975 now abandoned.

BACKGROUND OF THE INVENTION

1. Prior Art

In the process of the preparation of polyisocyanates which are used in conjunction with water in the production of polyurethane foams, polyoxyethylene polyols are generally end capped with monomeric isocyanates.

One of the monomeric isocyanates extensively used industrially in said end capping reaction is tolylene diisocyanate hereinafter referred to as TDI. TDI, as isocyanates in general, has been known for its physiologically detrimental effects and although generally only 2–3% by weight of free TDI is present in the polyoxyethylene polyol-TDI reaction product, which is used in foam manufacturing industry, it is sufficient to constitute a serious hazard to production line workers who are exposed to large volumes of the volatile isocyanate for prolonged periods of time.

Recent OSHA regulations have reduced the amount of free TDI permitted in the air from 0.02 p.p.m. to 0.005 ppm The prior art relating to means of removing residual free TDI from polyoxyethylene polyol-TDI reaction product is scarce which is attributable to the fact that only recently has a consciousness developed with regards to the deleterious effects of the presence of relatively minute quantities of unreacted TDI in said reaction product.

Nevertheless a number of expedients have been proposed in the past for rendering the isocyanates, and particularly volatile diisocyanates, utilizable. In particular, it has been proposed to react volatile di-functional isocyanates [having the general formula R-[NCO]$_2$ with polyfunctional alcohols (having the general formula X(OH$_n$), in a ratio —NCOeq/—OHeq of about 2:1.

Theoretically, that reaction should result in the production of a high molecular weight (and consequently essentially non-volatile) polyisocyanate containing as many —NCO isocyanic groups as there are hydroxyl groups contained in the polyalcohol, i.e. in the production of products of the type:

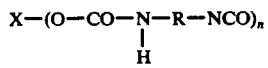

However, in practice, that result is not obtained. Using the aforesaid ratio, there still remain, in the final product, hazardous unreacted amounts of the starting volatile di-functional isocyanate and there are present compounds having a higher molecular weight than the theoretical molecular weight and which derive from the reaction of all the isocyanic groups of a same molecule of the same starting volatile difunctional isocyanate.

It is possible, by using —NCOeq/—OHeq ratios higher than 2:1, to reduce the formation of high molecular weight condensates. However, when such ratios are used, the amount of unreacted volatile diisocyanate contained in the reaction product is increased.

On the other hand, when —NCOeq/-OHeq ratios lower than 2:1 are used, the amount of unreacted volatile diisocyanate in the reaction product is reduced, but the content of high molecular weight condensates is increased.

According to the prior art, it is, in general, preferred to use —NCOeq/-OHeq ratios around 2:1 and to then remove the unreacted volatile isocyanate by chemical or physical means.

According to one prior art method, the unreacted volatile isocyanate is removed from the crude (total) reaction product by rapid distillation under vacuum. That procedure involves a number of drawbacks since, in order to insure a rapid distillation, it is necessary to operate at temperatures that give collateral reactions which (by reaction between isocyanic and urethane groups) result in the formation of allophanic acid esters and polymers having an isocyanate structure. The result is that the finished product obtained by that process is (as compared to the crude reaction product) strongly yellowed, more viscous, and has a higher molecular weight and a lower content of isocyanic group.

According to another prior art method, the crude (total) product of the reaction between the isocyanate and polyfunctional alcohol is treated with an aliphatic or cycloaliphatic hydrocarbon which is a selective solvent for the unreacted volatile diisocyanate. The treatment with the selective aliphatic or cycloaliphatic hydrocarbon must be carried out at a starting temperature of at least 80° C and at a final temperature of about 130° C to prevent precipitation of the high molecular weight polyisocyanate during extraction of the unreacted volatile isocyanate. Owing to the temperatures used, that procedure involves the same drawbacks as those mentioned previously.

According to another prior art method, the unreacted volatile diisocyanate is extracted from a solution of the crude (total) reaction product, in a solvent such as, for example, acetic acid esters, alkyl carbonates, ketones, chlorinated hydrocarbons which are, in general, the same as the solvents used as the liquid reaction medium, with mixtures of those solvents of the crude reaction product and aliphatic or cycloaliphatic hydrocarbons. The high molecular weight polyisocyanate is only slightly soluble in the aliphatic or cycloaliphatic hydrocarbons which show an affinity for both the unreacted volatile isocyanate and the solvents for the crude reaction product, so that, using this method it is possible to carry out the extraction of the unreacted volatile isocyanate at temperatures which avoid the collateral reactions mentioned hereinabove.

However, this last mentioned method is not free from technological difficulties. In practice, the mixture of solvents used for the extraction of the unreacted isocyanate from the crude reaction product must be selected in dependence on the nature of the polyisocyanate and used in a particular ratio of the solvent for the particular crude reaction product to the aliphatic or cycloaliphatic hydrocarbon which ratio must be maintained constant throughout the extraction. For example, if an excess of the solvent for the crude reaction product is used, there is a significant loss of high molecular weight polyisocyanate during the extraction, while use of an excess of the aliphatic or cycloaliphatic hydrocarbon results in the precipitation of the high molecular weight polyisocyanate in the form of crystals which obstruct and block the extraction apparatus.

Most recently a process for the obtention of a high molecular weight polyisocyanate has been disclosed in U.S. Pat. No. 3,883,577 where the reaction between the volatile diisocyanate and an active hydrogen containing compound is carried out in a solvent medium which has a strong affinity for the reaction product (high molecular weight polyisocyanate) but is only partly miscible with the hydrocarbon used as solvent for the extraction of the unreacted volatile diisocyanate and facilitates separation of the diisocyanate by being easily distillable without causing collateral reactions.

It may thus seem that the prior art has dealt with the problem of removal of unreacted TDI from polyisocyanates by primarily concentrating on either stoichiometrical adjustments or solvent extraction, both methods having as main drawback the inherent undesirable effect on the reaction products' molecular weight (and on crosslink density).

2. Objects of the Invention

It is therefore an object of the present invention to reduce the concentration of unreacted TDI present in polyisocyanates which are the reaction product of said TDI and polyoxyethylene polyols to as low a level as economically feasible and physiologically and therefore legally acceptable.

It is a further object of this invention to accomplish the removal of free TDI from polyisocyanate batches which does not require the use of solvent extraction techniques.

More particularly it is an object of this invention to provide a simple and efficient process for the removal of unreacted TDI from a high molecular weight polyisocyanate by contacting said polyisocyanate with molecular sieves.

These and other objects of the invention will become apparent as the description of this invention proceeds.

BRIEF DESCRIPTION OF THE INVENTION

This invention provides a system for the non-solvent extractive removal of toxic unreacted TDI from a high molecular weight polyisocyanate which is the reaction product of said TDI with polyoxyethylene glycol.

The system accomplishes said TDI removal by allowing said high molecular weight polyisocyanate to flow through a mildly heated column packed with absorbent molecular sieve (e.g. commercially available X-type zeolites) wherein the arylisocyanate is preferentially absorbed.

DETAILED DESCRIPTION OF THE INVENTION

This invention provides a method for the removal of unreacted TDI from a high molecular weight polyisocyanate which is the reaction product of said TDI with a polyoxyethylene glycol.

The polyurethane foam industry uses high molecular weight polyisocyanates as their so-called "prepolymers" in the preparation of their foams. Polyisocyanate prepolymers are generally the reaction product of isocyanates and polyols and specifically, as related to the present invention, of a mixture of 2,4 and 2,6 tolylenediisocyanate and polyethylene glycol. When these reactants are mixed at stoichiometric amounts i.e. 2.0 equivalents —NCO/1.0 equivalents —OH often in presence of a crosslinking agent such as trimethylol propane and/or a catalyst and are heated, the following reaction presumably takes place:

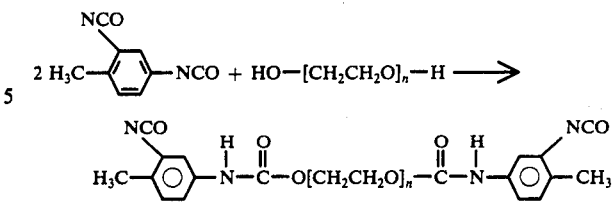

i.e. through polyurethane linkage formation a high molecular weight polyisocyanate is formed.

This "prepolymer" is later reacted with $H_2O$ through its —NCO functionality whereby $CO_2$ is formed; with the resulting —$NH_2$ group reacting with another —NCO group so that a urea linkage is established; thus the foam is formed.

The scope of this invention however is restricted to the high molecular polyisocyanate at its "prepolymer" stage. At that stage it is shipped to the foam manufacturing plants for eventual foaming. It is thus handled at a not necessarily strictly chemically oriented industrial environment by large numbers of workers in large volumes for prolonged periods of time. The content of previously discussed toxic TDI ranges at that stage from 2 to 3% a level which must be reduced for compliance with OSHA regulations which now restrict the maximum amount of free TDI in air to 0.005 ppm.

It has been known for some time that certain zeolites both naturally occuring and synthetic, have the property of separating organic compound molecules as a function of their molecular weight and/or atomic configuration. Reference to that effect is made to an article appearing in Quarterly Reviews, Vol. III, pp. 293–330 (1949), titled "Molecular Sieve Action of Solids" published by the Chemical Society (London).

These zeolites have crystalline structures containing a large number of small cavities interconnected by a number of still smaller holes or pores, the latter being of exceptional uniformity of size. Only molecules small enough to enter the pores can be absorbed, although not all molecules even though small enough to enter the pores, will be absorbed. An affinity of the molecule for the absorbent must be present. The pores may vary in diameter from 3–5 Angstrom units to 12–15 or more but it is a property of these zeolites, or molecular sieves, that for a particular sieve the pores are of substantially uniform size. Thus, in a program designed to aim at minimizing the unreacted TDI content in the high molecular weight polyisocyanate it was discovered that when said polyisocyanate was contacted with a specific molecular sieve the unreacted TDI content in it was drastically reduced, i.e. by amounts ranging from 50 to 99% of the original unreacted TDI.

More specifically, the high molecular weight polyisocyanate was allowed to flow through a heated column packed with an X-type zeolite with a pore size of 6–8A and having a ratio of $NA_2O/Al_2O_3/SiO_2$ of 1.0/1.0/2.5; a crystalline powder with a distinctive X-ray diffraction pattern commercially available in quantity. The effluent was analyzed for free TDI content and it was noted that a reduction of TDI content in the order of 67% had occured, without an accompanying change in the polymer's viscosity.

Although in the present invention a column has been employed, other geometries may be used for treatment as for example adding the molecular sieves to polyisocyanate batch and then removing said sieves by filtration or centrifugation. Also, before treatment with the molecular sieves the polyisocyanate may be slightly heated to decrease its viscosity hence decreasing its dwell time in the column.

Desorption of the material from the molecular sieves may be brought about by purging first with a suitable solvent e.g. anhydrous methanol to remove any residual polyisocyanate and then with a suitable inert gas followed by reactivation heating.

Although in the present invention TDI was used as the aryl isocyanate, trimethylolpropane as the crosslinking trihydric alcohol, and polyethylene glycol as the polyoxyalkylene polyol these compounds are in no way intended to be limiting. The principles involved in the novel method of removing unreacted monomeric isocyanate from a polyisocyanate apply as well to polyisocyanates which are the reaction product of a wide variety of monomeric isocyanates, trihydric alcohols, and polyoxyalkylene polyols some of which are enumerated as follows.

The monomeric isocyanates used for capping the polyoxyalkylene polyols include isothiocyanates and isocyanates such as PAPI (a polyaryl polyisocyanate as defined in U.S. Pat. No. 2,683,730), tolylene diisocyanate, triphenylmethane-4,4',4'', -triisocyanate, benzene-1,3,5-triisocyanate, toluene-2,4,6-triisocyanate, diphenyl-2,4,4'-triisocyanate, hexamethylene diisocyanate, xylene diisocyanate, chlorophenylene diisocyanate, diphenylmethane-4,4'-diisocyanate, naphthalene-1,5-diisocyanate, xylene-alpha, alpha'-diisothiocyanate, 3,3'-dimethyl-4,4'-biphenylene diisocyanate, 3,3'-dimethoxy-4,4'-biphenylene diisocyanate, 2,2',5,5'-tetramethyl-4,4'-biphenylene diisocyanate, 4,4'-methylenebis (phenylisocyanate), 4,4'-sulfonylbis (phenylisocyanate), 4,4'-methylene di-orthotolylisocyanate, ethylene diisocyanate, ethylene diisothiocyanate, trimethylenediisocyanate, dicyclohexyl methane-4,4'diisocyanate, isophorone diisocyanate, 1,6-hexamethylene diisocyanate, 2,2,4-trimethyl-1,6-hexane diisocyanate, and the like. Mixtures of any one or more of the above mentioned organic isothiocyanates or isocyanates may be used as desired.

As the crosslinking polyol component preferably a trihydric alcohol is used such as glycerol, trimethylolethane, trimethylol propane and the like.

The polyoxyalkylene polyols may be selected from the group comprising the reaction products derived from the polymerization of ethylene oxide or propylene oxide in the presence of a polyfunctional starter compound such as water, ethylene glycol, glycerol, pentaerythritol, sucrose and the like.

The following examples, while in no way intended to be limiting, will aid in the understanding of this invention.

EXAMPLE 1

A typical polyisocyanate was prepared by reacting polyethylene glycol and trimethylol propane with tolylene diisocyanate at a temperature of about 50° to 60° C.

After storing the reaction product for at least 24 hours, the residual free tolylene diisocyanate content was determined and ranged from 2.0% to 3.0%.

EXAMPLE 2

Another typical polyisocyanate was prepared by the reaction of polyethylene glycol with tolylene diisocyanate at a temperature of 35° to 50° C. This time heating was continued for several hours at 60° C. The residual free TDI content in the system, depending on time during post reaction heating time at which sample was taken, ranged from 0.8 to 3.0%.

EXAMPLE 3

A column 2.5 cm in diameter and 80.0 cm long was packed with 105 g. of type X molecular sieves which had been dried prior to use for two hours at 700° F. This column was then mounted in a vertical Lundberg furnace, brought to and held at a temperature of 50° C, followed by the addition of 130.0 g. of the polyisocyanate prepared as described in Example 1.

The original unreacted TDI content of said polyisocyanate as determined by solvent extraction and UV absorption spectrometry technique was 2.2%. Four successive fractions of the polyisocyanate which had passed through the column described above had their free TDI content determined by the same technique as that used for the original untreated polyisocyanate and the results were as follows: 0.7%, 1.0%, 1.3%, and 1.0% i.e. 1.0% ± 0.2, which amounts to an approximate reduction in unreacted TDI content in the order of 55%. The initial viscosity was about 25,000 centipoises at 22° C and the eluant fractions' viscosities ranged from 25,000 to 40,000 centipoises.

Example 4

A similar column as that described in Example 3 was packed with 97.6 g of X-type molecular sieve. The column was mounted in a vertical Lundberg furnace, brought to and held at 70°-75° C followed by the addition of 111.0 g the polyisocyanate prepared as described in Example 2.

The original unreacted TDI content of said polyisocyanate as determined by solvent extraction and UV absorption spectrometry was 0.9%. Five successive fractions of the polyisocyanate which had passed through the column described previously had their free TDI content determined by the same technique as that used for the original untreated polyisocyanate and the results were as follows: 0.4%, 0.2%, 0.4%, 0.2% i.e. 0.3% ± 0.1 which amounts to an approximate reduction in TDI content of 67%. No appreciable viscosity change was observed following passage of the polyisocyanate through the heated column.

What is claimed is:

1. A method of reducing the residual unreacted tolylene diisocyanate content in the prepolymer reaction product of toluene diisocyanate with a polyoxyalkylene polyol comprising allowing said prepolymer to flow through a column packed with absorbent type X zeolite molecular sieves.

2. A method of reducing the residual unreacted tolylene diisocyanate content in the prepolymer reaction product of toluene diisocyanate with a polyoxyalkylene polyol comprising allowing said prepolymer to be mixed with absorbent type X zeolite molecular sieves.

3. The method according to claim 1 wherein the amount by which the unreacted TDI is reduced ranges from 50 to 99% of the original unreacted diisocyanate.

4. The method according to claim 1 wherein said prepolymer is allowed to flow through said type X zeolite molecular sieve packed column at temperatures of about 20 to 100° C.

5. The process according to claim 4 wherein said packed column is at a temperature of 40 and 85° C.

6. The method according to claim 2 wherein said mixing between said prepolymer and said molecular sieves is carried out by adding said molecular sieves to the prepolymer and mixing at temperatures of 50° to 75° C, followed by removal of molecular sieves by filtration.

7. The method according to claim 2 wherein molecular sieve removal is accomplished by centrifugation.

8. The method according to claim 1 wherein said prepolymer is the reaction product of a polyoxyalkylene polyol, toluene diisocyanate and polyhydric alcohol.

9. The method according to claim 8 wherein said polyoxyalkylene polyol is polyethylene glycol, and said polyhydric alcohol is trimethylol propane.

10. The method according to claim 1 wherein said molecular sieves comprise X-type zeolites having a ratio of $Na_2O:Al_2O_3:SiO_2::1.0:1.0:2.5$.

11. The method according to claim 2 wherein said molecular sieves comprise X-type zeolites having a ratio of $Na_2O:Al_2O_3: SiO_2:: 1.0:1.0:2.5$.

12. A method of reducing the amount of unreacted monomeric isocyanate in a urethane prepolymer formed by reacting the hydroxyl groups of a polyoxyalkylene polyol with said monomeric isocyanate, said method comprising admixing said prepolymer with absorbent type X zeolite molecular sieves.

13. A method as in claim 12 wherein the polyoxyalkylene polyol is polyoxyethylene glycol.

14. A method as in claim 12 wherein the prepolymer is formed by capping a mixture of polyoxyethylene glycol and a monomeric trihydric alcohol with a monomeric isocyanate.

15. A method as in claim 14 wherein the trihydric alcohol is trimethylolpropane or trimethylolethane.

16. A method as in claim 12 wherein the polyoxyalkylene polyol is a polyoxyethylene/polyoxypropylene copolymer.

* * * * *